(12) United States Patent
Drew

(10) Patent No.: US 8,016,205 B2
(45) Date of Patent: Sep. 13, 2011

(54) THERMOSTAT WITH REPLACEABLE CARBON MONOXIDE SENSOR MODULE

(75) Inventor: David Scott Drew, St. Louis, MO (US)

(73) Assignee: Emerson Electric Co., St. Louis, MO (US)

( * ) Notice: Subject to any disclaimer, the term of this patent is extended or adjusted under 35 U.S.C. 154(b) by 421 days.

(21) Appl. No.: 12/370,272

(22) Filed: Feb. 12, 2009

(65) Prior Publication Data

US 2010/0200664 A1    Aug. 12, 2010

(51) Int. Cl.
G05D 23/00 (2006.01)
G08B 21/00 (2006.01)

(52) U.S. Cl. ............. 236/94; 62/127; 340/632; 700/276

(58) Field of Classification Search ............ 236/94; 62/127, 129; 340/632; 700/276
See application file for complete search history.

(56) References Cited

U.S. PATENT DOCUMENTS

| 4,007,456 A * | 2/1977 | Paige et al. ............... 340/507 |
| 5,280,273 A | 1/1994 | Goldstein ............... 340/632 |
| 5,793,296 A | 8/1998 | Lewkowicz ............... 340/632 |
| 6,484,951 B1 | 11/2002 | Mueller ............... 237/2 A |
| 6,578,770 B1 | 6/2003 | Rosen ............... 236/49.3 |
| 6,998,991 B1 | 2/2006 | Goldstein et al. ............... 340/628 |
| 2008/0182506 A1 * | 7/2008 | Jackson et al. ............... 454/354 |

* cited by examiner

Primary Examiner — Marc Norman
(74) Attorney, Agent, or Firm — Harness, Dickey & Pierce, P.L.C.; Kevin Pumm

(57) ABSTRACT

A thermostat is provided that includes a peripheral edge that, at least in part, defines an opening in the thermostat. The thermostat further includes a carbon monoxide sensor capable of sensing the presence of carbon monoxide gas in the ambient air near the thermostat, and providing a measurable output value that is indicative of the level of carbon monoxide gas. The thermostat also includes a replaceable battery that applies a voltage to the carbon monoxide sensor. The thermostat further includes a microprocessor disposed on a circuit board. The circuit board, sensor and battery are together disposed on or in the thermostat. The circuit board is configured to establish an electrical connection with the carbon monoxide sensor and the battery. The microprocessor is configured to periodically read the carbon monoxide sensor output, and to activate an audible alarm in a continuous manner to indicate an emergency upon detecting a carbon monoxide level that exceeds a predetermined value.

15 Claims, 6 Drawing Sheets

THERMOSTAT WITH REPLACEABLE CARBON MONOXIDE SENSOR MODULE

FIELD

The present disclosure relates to thermostats, and more particularly to sensors within digital thermostats for sensing carbon monoxide in occupied environments.

BACKGROUND

The statements in this section merely provide background information related to the present disclosure and may not constitute prior art.

Although smoke detectors are typically installed throughout the home, carbon monoxide detectors are often only installed in a basement or utility room that encloses a furnace or water heater. While useful for their intended purpose of detecting carbon monoxide in the basement, such installations do not monitor the spaces occupied by persons in the home. This would require the installation within the occupied space of an additional sensor, which some occupants consider to be unsightly as well as costly.

SUMMARY

The present application discloses various embodiments of a wall-mounted thermostat that includes a replaceable carbon monoxide sensor that is independent from but located with or on a thermostat. In one embodiment, a thermostat is provided that includes a housing having at least one peripheral edge that, at least in part, defines an opening that provides access to the interior space of the thermostat. The thermostat further includes an access cover for covering the opening in the thermostat. The access cover is removably attached to the thermostat, to thereby allow the access cover to be removed to permit access to the interior space of the thermostat.

The thermostat further includes a carbon monoxide sensor capable of sensing the presence of carbon monoxide gas in the ambient air near the thermostat, and providing a measurable output value that is indicative of the level of carbon monoxide gas. The thermostat also includes a replaceable battery that applies a voltage to the carbon monoxide sensor. The thermostat further includes a microprocessor disposed on a circuit board that is secured within the interior space of the thermostat, adjacent the opening. The circuit board is configured to establish an electrical connection with the carbon monoxide sensor and the battery, which electrical connection permits the microprocessor to monitor the output value of the carbon monoxide sensor that has been inserted and/or connected to the circuit board. The microprocessor is configured to periodically read the carbon monoxide sensor output, and is further configured to activate an audible alarm in a continuous manner to indicate an emergency upon detecting an output value from the carbon monoxide sensor that exceeds a predetermined value.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

DETAILED DESCRIPTION

Figure 1:
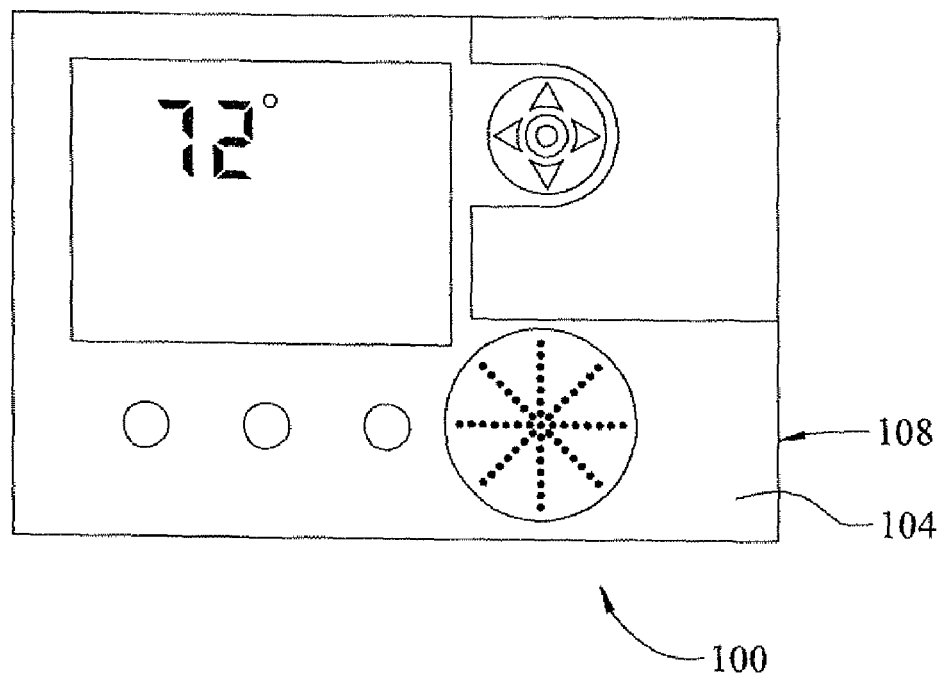
FIG. 1 is a front plane view of one embodiment of a thermostat according to the principles of the present application.

The following description is merely exemplary in nature and is not intended to limit the present disclosure, application, or uses. It should be understood that throughout the drawings, corresponding reference numerals indicate like or corresponding parts and features.

Figure 2:
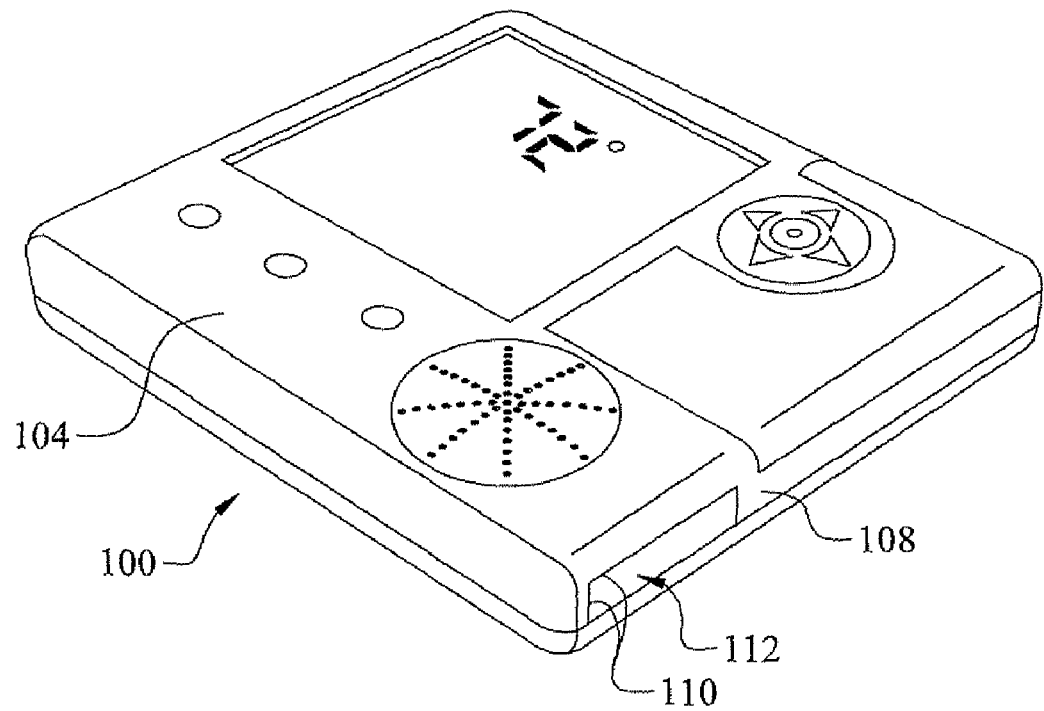
FIG. 2 is a perspective view of the thermostat of FIG. 1.
Figure 3:
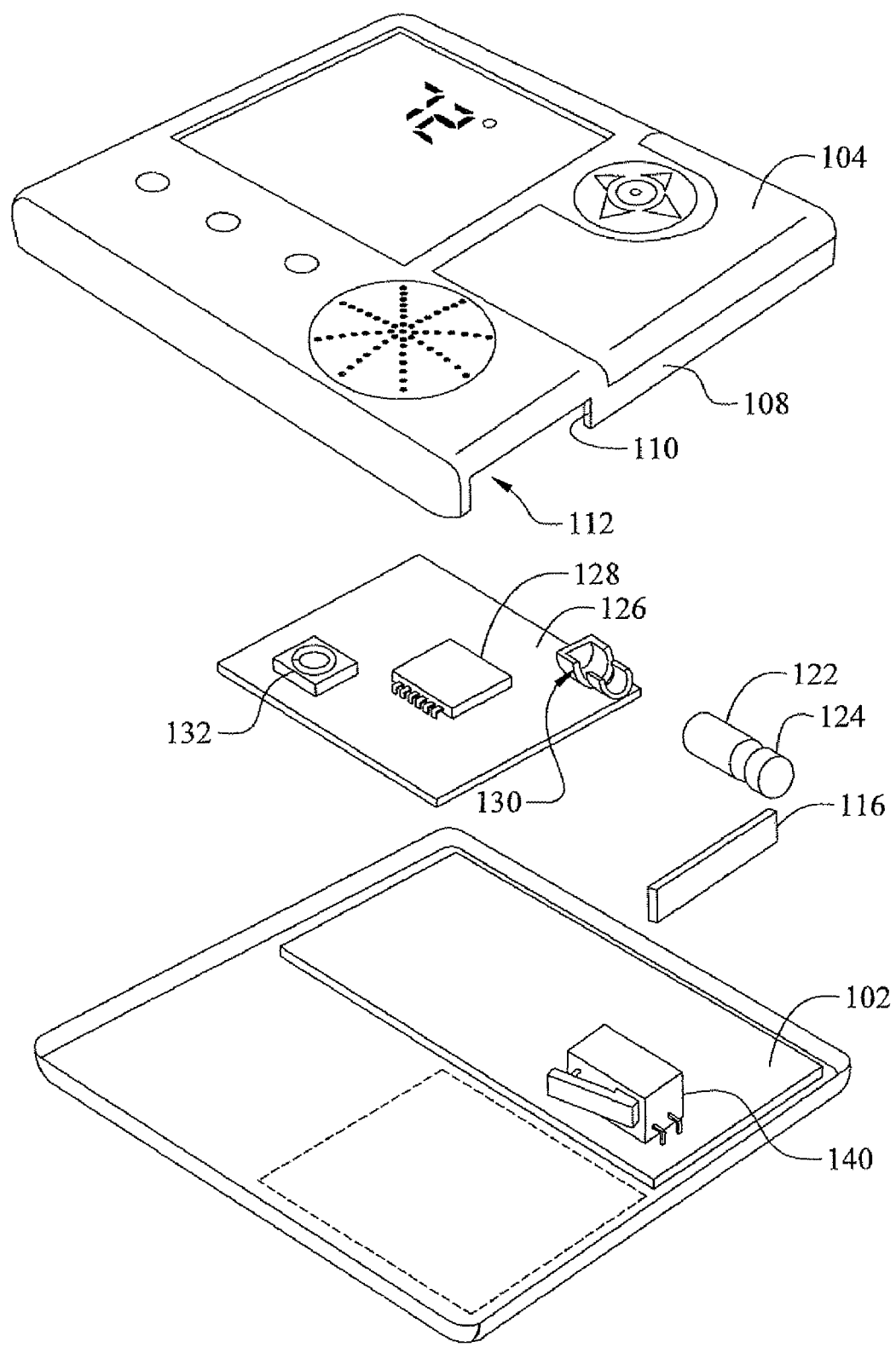
FIG. 3 is an exploded assembly view of the carbon monoxide sensor components and thermostat of FIG. 1.

Referring to FIGS. 1-3, a first embodiment of thermostat 100 is shown. The thermostat 100 includes a housing 104 having at least one peripheral portion 108 that, at least in part, defines an opening 110 in the thermostat 100, which provides access to the interior space 112 of the thermostat (See FIG. 3). The thermostat 100 further includes an access cover 116 for covering the opening 110 in the thermostat 100. The access cover 116 is removably attached to the thermostat 100, to thereby allow the access cover 116 to be removed to permit access to the interior space 112 of the thermostat 100.

The thermostat 100 further includes a carbon monoxide sensor 122 capable of sensing the presence of carbon monoxide gas in the ambient air near the thermostat 100. The carbon monoxide sensor 122 is configured to provide a measurable output value that is indicative of the level of carbon monoxide gas. The thermostat 100 also includes a replaceable battery 124 that applies a voltage to the carbon monoxide sensor 122. The thermostat 100 further includes a microprocessor 128 disposed on a circuit board 126 that is secured within the interior space 112 of the thermostat 100, adjacent the opening 110 and between the base portion 102 and thermostat cover 104. The circuit board 126 is configured to establish an electrical connection with the carbon monoxide sensor 122 and the battery 124, which electrical connection permits the microprocessor 128 to monitor the output value of the carbon monoxide sensor 122 that has been inserted and/or connected to the circuit board 126. The microprocessor 128 is configured to periodically read the carbon monoxide sensor output, and is further configured to activate a speaker 132 to provide an audible alarm in a continuous manner to indicate an emergency upon detecting an output value from the carbon monoxide sensor 122 that exceeds a predetermined value. The microprocessor 128 may also activate the emergency alarm where the sensor's output value changes by at least a 50 percent over a prior sensor output value received within a period of time of between about 15 to 90 minutes. The microprocessor 128, which is in communication with the carbon monoxide sensor 122, thus provides an audible emergency alarm signal to alert an occupant of the presence of a harmful level of carbon monoxide gas (a harmful level of carbon monoxide gas may be the presence of at least 300 parts per million of carbon monoxide gas, for example).

This embodiment of a thermostat 100 with an integral or co-located carbon monoxide sensor 122 is advantageous because it is configured to provide an emergency alarm upon detecting a harmful level of carbon monoxide gas in the ambient air surrounding the thermostat 100 where the occupants are. Positioning the carbon monoxide sensor 122 on the thermostat 100 ensures that the sensor is positioned properly to sense the level of carbon monoxide in the space that is being occupied, rather than at the location of a furnace or water heater in a basement or garage. The carbon monoxide sensor 122 is also protected by the thermostat housing 104 against exposure to water or humidity that could cause the carbon monoxide sensor 122 to become inoperable or provide an inaccurate reading. Accordingly, the thermostat 100 provides the advantage of including an integral or co-located carbon monoxide sensor 122 for detecting the presence of carbon monoxide within the space that is being occupied by humans, rather than that of a basement or separate furnace/utility room. The thermostat 100 and co-located carbon monoxide sensor 122 also provide an audible emergency alarm which can be easily heard within the space being occupied, unlike carbon monoxide sensors located in a basement or separate furnace/utility room which cannot be readily heard. The inclusion of the carbon monoxide sensor 122 within the thermostat 100 would also provide a less costly and more appealing alternative to a stand-alone sensor. Also, the location of the sensor with or on the thermostat provides easy access to the carbon monoxide sensor for inspection, periodic operational testing, and replacement by the user, and would be more easily replaced by elderly persons than a separate carbon monoxide sensor mounted on a wall that may require the aid of a ladder.

Preferably, the carbon monoxide sensor 122 provides an output value that changes in response to sensing an increase in the presence of carbon monoxide gas. For example, the carbon monoxide sensor 122 may be an electrochemical sensor of the Colorimetric type that senses the build-up of carbon monoxide over time and increases in resistance in response to an increase in the level of carbon monoxide gas concentration. Such a sensor could be a Colorimetric sensor detector, which measures the build-up of carbon monoxide over time, and may take up to 48 hours to reset. For example, where a typical carbon monoxide sensor may have a low resistance when sensing less than 100 parts per million of carbon monoxide over a 90 minute period, such resistance could rapidly increase by a factor of 3 to 1 when exposed to a carbon monoxide presence of 300 parts per million (ppm) over a 30 to 90 minute period.

The carbon monoxide sensor 122 may also be a Metal Oxide Semiconductor (MOS) sensor, which may be made of a tin dioxide ($SnO_2$) on a sintered alumina ceramic, for example. One example of a MOS carbon monoxide sensor may be a CGS-200 CO sensor manufactured by City Technology. In the case of a Metal Oxide Semiconductor (MOS) carbon monoxide sensor, the electrical conductivity is low in clean air, but the conductivity increases when exposed to a carbon monoxide presence. The MOS carbon monoxide sensor accordingly has a conductivity output that increases (or a resistance that decreases) with carbon monoxide level, as opposed to the electrochemical sensor which has a resistance that increases with carbon monoxide level. The MOS carbon monoxide sensors offer the ability to detect low (0-100 ppm) concentrations of carbon monoxide gases over a wide temperature range. Accordingly, the measurable output value of the replaceable carbon monoxide sensor 122 may be a resistance value that increases with an increase in the level of carbon monoxide, or may be a resistance value that decreases with an increase in the level of carbon monoxide. The measurable output value of the replaceable carbon monoxide sensor 122 may also be a voltage drop across the replaceable carbon monoxide sensor 122, where the voltage may change by at least 50 percent within a period of time of between about 15 to 90 minutes upon exposure to a level of carbon monoxide of at least 300 parts per million. The carbon monoxide sensor 122 may also comprise an electrolyte solution, such as a water based gel MicroSir sensor manufactured by Quantum Group, as disclosed in U.S. Pat. No. 6,998,991.

However, it has been observed that carbon monoxide sensors may undergo changes in resistance due to general ageing, even in a mild environment. Electro-chemical sensors may dry out, or may erode as a result of chemical vapors, e.g., chlorines commonly found in household bleaches. Over time, a carbon monoxide sensor may gradually increase in resistance sufficient to cause a false shut-down of a furnace system. On the other hand, the resistance of a carbon monoxide sensor may diminish gradually over time due to other circumstances, possibly to such a low level that it might not trip a shut-down of a heating system if a harmful level of carbon monoxide gas were to occur. Some sensors encounter an output increase with an increase in humidity, and sensor output may fall to zero even in the presence of gas when humidity drops to very low levels. Environmental exposure of the sensor and the effects of humidity on sensor output can lead to difficulties in the interpretation of positive readings of the sensor. Accordingly, the output of such carbon monoxide sensors will not be reliable after a given period of time of continuous use.

To address this concern, the first embodiment of a thermostat 100 includes a replaceable carbon monoxide sensor 122 that is configured to be removably inserted through the opening 110 leading into the interior space 112 of the thermostat 100. The thermostat 100 also includes a replaceable battery 124 that applies a voltage to the replaceable carbon monoxide sensor 122, where the battery 124 is also configured to be removably inserted through the opening 110 in the thermostat 100. The thermostat 100 further includes a microprocessor 128 disposed on a circuit board 126 that is secured within the interior space 112 of the thermostat 100, adjacent the opening 110. The thermostat 100 has a separate circuit (not shown) that operates independent of the stand-alone circuit board 126 and microprocessor 128, which may be removed or replaced without interfering with the operation of the thermostat 100. The circuit board 126 includes a receptacle 130 configured to releasably receive the replaceable carbon monoxide sensor 122 and the battery 124 in a manner that establishes electrical connection between the carbon monoxide sensor 122, battery 124 and the circuit board 126.

The replaceable carbon monoxide sensor 122 is configured to provide a signal or a measurable output value that is indicative of the level of carbon monoxide presence in the ambient air surrounding the thermostat 100, where the output or measurable value changes over time due to the nature of the sensor. With Electro-chemical or Metal Oxide Semiconductor (MOS) carbon monoxide sensors, continuous use of the sensor over an extended period of time causes the sensor's nominal output value to change substantially over time. Since a certain conductivity or resistance level of the sensor is typically relied upon for indicating the presence of a harmful level of carbon monoxide gas (such as 400 parts per million, for example), a substantial change in the sensor's conductivity or resistance over time would accordingly cause the replaceable carbon monoxide sensor 122 to become subject to providing output values that would be unreliable after a given time period of use. Similarly, the resistive value of some carbon monoxide sensors may change relative to the ambient temperature that the sensor is exposed to. Since a certain resistance level of the sensor is typically relied upon for indicating the presence of a harmful level of carbon monoxide gas, a shift in the sensor's resistance due to a warm ambient temperatures in high ceiling areas, or cooler ambient temperatures in basement areas could accordingly cause the replaceable carbon monoxide sensor 122 to become subject to providing inconsistent or unreliable output values.

Accordingly, the microprocessor 128 on the circuit board 126 is configured to monitor the carbon monoxide sensor 122 and to responsively activate a speaker 132 to provide a service alarm when the microprocessor 128 detects that the replaceable carbon monoxide sensor 122 has exceeded a predetermined duration of use. The predetermined duration of use may be, for example, a period of at least 4 years. The microprocessor 128 thereby prompts a user to replace the replaceable carbon monoxide sensor 122 with a new carbon monoxide sensor (not shown). The access cover 116 is releasably attached to the thermostat 100 to permit access to the interior space 112, to thereby allow for the removal of the battery 124 and the replaceable carbon monoxide sensor 122 for replacement thereof. In the thermostat 100 shown in FIGS. 1-3, the replaceable carbon monoxide sensor 122, battery 124 and stand-alone circuit board 126 are located completely within the interior space 112 of the thermostat 100. This provides the advantage of a thermostat 100 including an integral or co-located replaceable carbon monoxide sensor 122 for detecting the presence of carbon monoxide within the space that is being occupied by humans (rather than that of a basement or separate furnace/utility room), which also prompts the user to replace the replaceable carbon monoxide sensor 122 upon determining that the carbon monoxide sensor is no longer reliable, such that the occupants are provided with reliable protection against the danger of carbon monoxide gas within the home.

The thermostat 100 with a replaceable carbon monoxide sensor 122 also provides an additional function beyond that of the sensor's function of detecting a harmful level of carbon monoxide gas, in locating the carbon monoxide sensor 122 in a location where ambient temperatures will be maintained relatively constant by the thermostat 100. By positioning the carbon monoxide sensor within the thermostat. Unlike ceiling areas where temperatures tend to increase as heat rises, or basement areas that tend to be cooler or subject to humidity, the present carbon monoxide sensor 122 located within the thermostat 100 is exposed to a relatively consistent ambient temperature that is maintained by the thermostat 100. In this manner, the resistive output of the carbon monoxide sensor 122 is more consistent, and less likely to be affected by temperature. Since a certain resistance level of the sensor is typically relied upon for indicating the presence of a harmful level of carbon monoxide gas, the thermostat 100 of the present invention provides the added function of ensuring that the carbon monoxide sensor 122 is exposed to a consistent ambient temperature, so as to provide for more reliable sensor operation.

Additionally, the thermostat 100 having a replaceable carbon monoxide sensor 122 provides an additional function beyond that of the sensor's function of detecting a harmful level of carbon monoxide gas. The thermostat 100 is configured to provide the added function of permitting heating operation only when the carbon monoxide sensor 122 and battery 124 are installed, as explained below.

The thermostat 100 may comprise a mechanical switch activated by displacement of a lever 140, which is positioned within the interior space 112 of the thermostat, such that the lever 140 closes the switch only when the carbon monoxide sensor 122 and battery 124 are installed or received within the connector 130. Similarly, the switch could comprise a photo-optic emitter and collector positioned on opposite sides of the battery, for example, which would activate a switch when the battery is present between the emitter and collector. Alternatively, the thermostat 100 may employ a lever 140 that is displaced upon installation of the carbon monoxide sensor 122 and battery 124, where the cover 116 can only be attached upon displacement of the lever 140. The cover 116 could then cause a switch or electrical connection to occur upon attachment to the thermostat 100.

In the thermostat embodiment 100 shown in FIG. 3, the lever 140 preferably establishes electrical connection between the battery 124 and a thermostat control circuit associated with a circuit board 142. In this manner, the thermostat 100 would accordingly sense the presence of a voltage via the lever 140 when a battery 124 is received within the connector 130. When the carbon monoxide sensor 122 and battery 124 are installed (or alternatively when access cover 116 is attached), a switch or electrical connection occurs, which establishes a voltage that is detected by the control circuit associated with the circuit board 142 for controlling the thermostat's operation. The thermostat 100 enables heating operation only when this voltage is present and detected by the circuit board 142. Without installation of the carbon monoxide sensor 122 and battery 124, the disabled switch or lack of a connection would cause the thermostat to be incapable of operating the heating system. This ensures that a fuel-fired heating system would only be operated when a carbon monoxide sensor 122 and battery 124 have been installed, to provide for proper monitoring of carbon monoxide that may be produced by the fuel-fired heating system. Similarly, where the installed battery voltage is below a minimum detectable level, the thermostat control circuit associated with the circuit board 142 for controlling the thermostat 100 is configured to display a low battery indication and alter the temperature setting of the thermostat 100. The altered temperature setting may be a setting of 60 degrees Fahrenheit, for example, which would urge an occupant to check the thermostat and discover the display of a low level condition for the carbon monoxide sensor battery 124. Where the thermostat 100 does not detect the presence of a sufficient voltage via the electrical connection to the circuit board 142, the thermostat would not operate the heating system. This ensures that a fuel-fired heating system would only be operated when the battery 124 associated with the carbon monoxide sensor 122 has a sufficient voltage level to provide for proper monitoring of carbon monoxide that may be produced by the fuel-fired heating system.

Accordingly, the thermostat 100 and replaceable carbon monoxide sensor 122 provide an additional function beyond that of the sensor's function of detecting a harmful level of carbon monoxide gas, in preventing operation of a heating system that could produce carbon monoxide gas unless a carbon monoxide sensor 122 and battery 124 with a sufficient voltage level are installed. This ensures that the heating system will only be operated during periods when the carbon monoxide sensor is present and operating, to thereby monitor for carbon monoxide that may be produced by the fuel-fired heating system, which function is not provided by other commercially available carbon monoxide sensors.

In the above embodiment, the microprocessor 128 may be further configured to activate an audible service alarm output upon detecting that the battery level is below a predetermined threshold. While the thermostat 100 depicted in FIGS. 1-2 shows the replaceable carbon monoxide sensor 122 as being removable, alternatively, the circuit board 126, the replaceable carbon monoxide sensor 122 and battery 124 may all be removable through the opening 110, to thereby permit replacement of both the circuit board 126 and carbon monoxide sensor 122 together.

In an alternate embodiment, a thermostat may be provided that includes a microprocessor 128 disposed on a circuit board 126 (within the interior of the thermostat), which periodically reads the output value of the replaceable carbon monoxide sensor 122 and stores at least one output value of the carbon monoxide sensor 122 in a memory. In some embodiments, the microprocessor 128 responsively activates a service alarm when the microprocessor 128 detects that the sensor output value has changed by more than a predetermined amount over at least one previously stored sensor output value.

Figure 4:
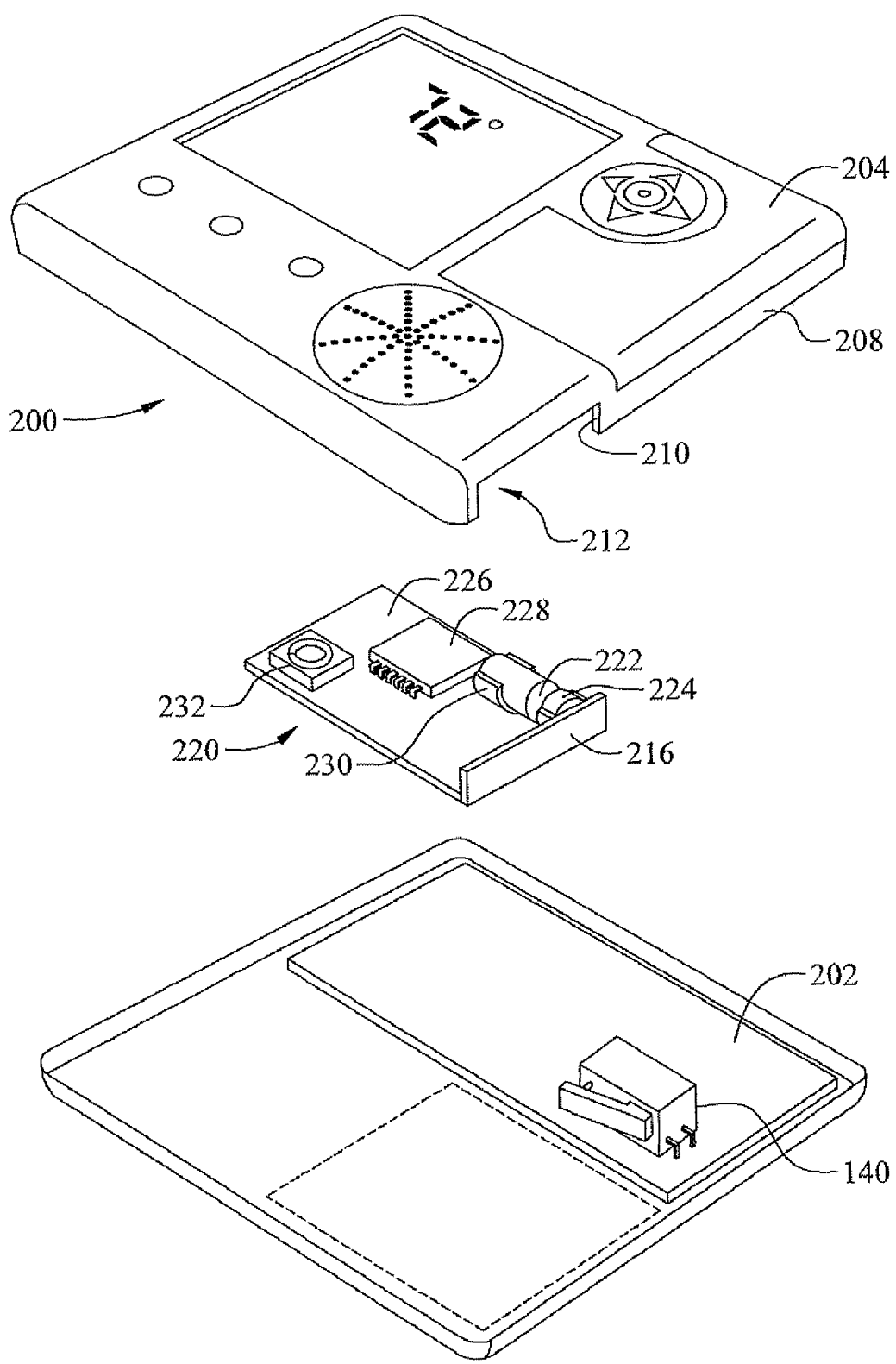
FIG. 4 is an exploded assembly view of the carbon monoxide sensor components and thermostat of a second embodiment according to the principles of the present application.

In a second embodiment shown in FIG. 4, the thermostat 200 includes a housing 204 having at least one peripheral edge 208 that defines, at least in part, an opening 210 in the thermostat 200 which provides access to the interior space 212 of the thermostat 200. The thermostat 200 further includes a replaceable carbon monoxide sensor module 220 that is disposed within the interior space 212 of the thermostat 200. The replaceable carbon monoxide sensor module 220 is configured to be removably received within the thermostat 200 through the opening 210. The replaceable carbon monoxide sensor module 220 includes a circuit board 226 having a connector or receptacle 230 thereon, a replaceable battery 224 configured to be releasably received within the receptacle 230, and a replaceable carbon monoxide sensor 222 configured to be releasably received within the receptacle 230 in a manner that establishes electrical connection between the battery 224, the carbon monoxide sensor 222 and the circuit board 226. The replaceable carbon monoxide sensor 222 provides a measurable output value that is indicative of the level of carbon monoxide gas in the ambient air surrounding the thermostat 200. The nature of the replaceable carbon monoxide sensor 222 is such that continuous use of the sensor over an extended period of time causes the sensor's nominal output value to change substantially over time. The replaceable carbon monoxide sensor module 220 further includes a microprocessor 228 disposed on the circuit board 226 that is configured to activate a speaker 232 to provide continuous audible alarm to indicate an emergency upon detecting a sensor output value indicative of a harmful level of carbon monoxide gas (a harmful level of carbon monoxide gas may be the presence of at least 300 parts per million of carbon monoxide gas, for example). The microprocessor 228 is also configured to monitor the replaceable carbon monoxide sensor 222 and to activate an intermittent audible service alarm when the replaceable carbon monoxide sensor 222 has exceeded a predetermined duration of use, to thereby prompt a user to remove and replace the replaceable carbon monoxide sensor module 220. The predetermined duration of use may be, for example, a period of at least 4 years.

Accordingly, the microprocessor 228 thereby prompts a user to replace the replaceable carbon monoxide sensor module 220 with a new carbon monoxide sensor module 220. The cover 216 on the carbon monoxide sensor module 220 is releasably attached to the thermostat 200 to permit access to the interior space 212, to thereby allow for the removal of the battery 224 and the replaceable carbon monoxide sensor module 220 for replacement thereof. In the thermostat 200 shown in FIG. 4, the replaceable carbon monoxide sensor module 220 is located completely within the interior space 212 of the thermostat 200. This provides the advantage of including an integral or co-located replaceable carbon monoxide sensor module 220 for detecting the presence of carbon monoxide within the space that is being occupied by humans (rather than that of a basement or separate furnace/utility room), which also prompts the user to replace the replaceable carbon monoxide sensor module 220 upon determining that the carbon monoxide sensor 222 is no longer reliable, such that the occupants are provided with reliable protection against the danger of carbon monoxide gas within the home.

Figure 5:
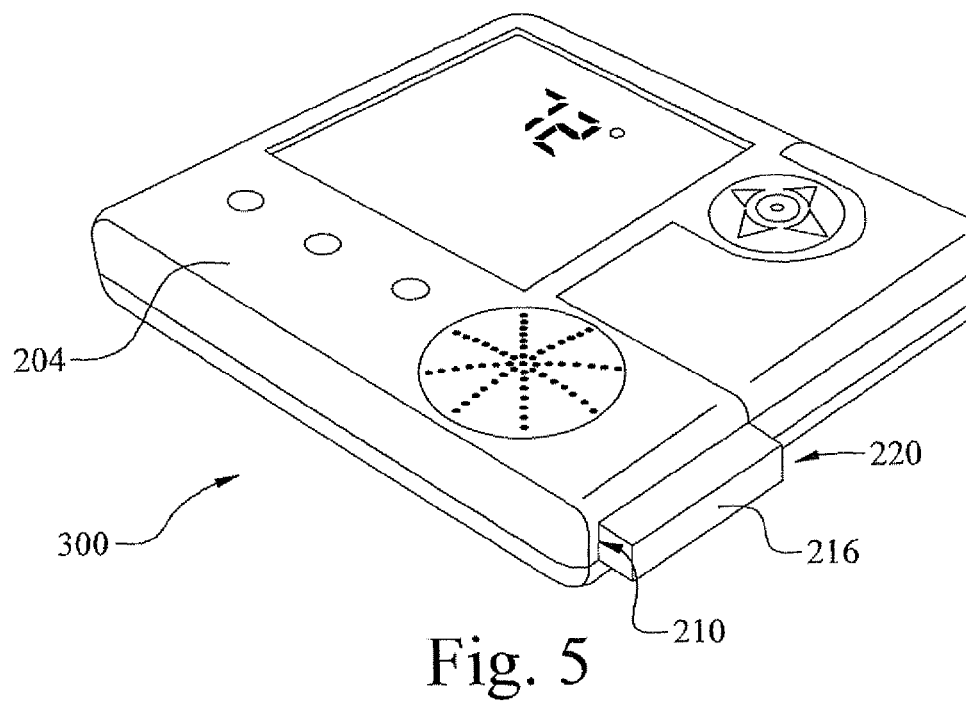
FIG. 5 is a perspective view of the carbon monoxide sensor components and thermostat of a third embodiment according to the principles of the present application.

In the second embodiment, the microprocessor 228 may be further configured to activate an audible service alarm upon detecting that the battery level is below a predetermined threshold. The thermostat 200 that is depicted in FIG. 4 shows the replaceable carbon monoxide sensor module 220 with a carbon monoxide sensor 222 and battery 224 that are together removably received through the opening 210 within the thermostat 200. Alternatively, a third embodiment of a thermostat 300, as shown in FIG. 5, may have a portion of the replaceable carbon monoxide sensor module 220, and the cover portion 216 attached thereto, that extend outside of the opening 210 and protrude from the thermostat housing 204, which provides a grip portion that can aid a user in the replacement of the carbon monoxide sensor module 220.

Figure 6:
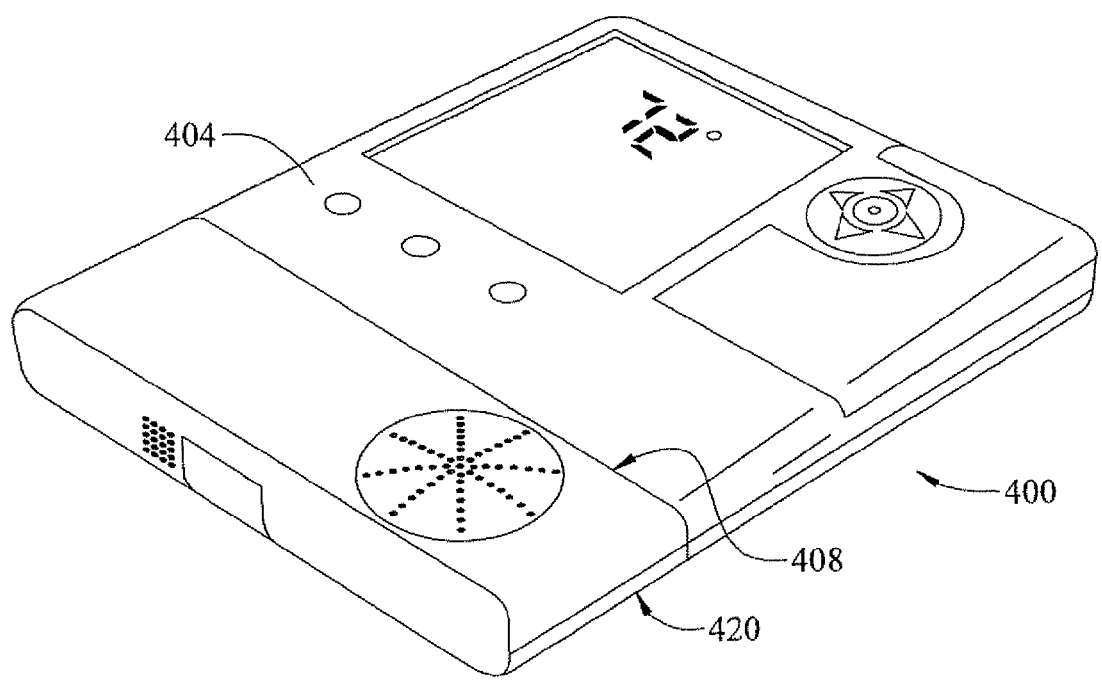
FIG. 6 is a perspective view of the carbon monoxide sensor components and thermostat of a fourth embodiment according to the principles of the present application.

In a fourth embodiment shown in FIG. 6, the thermostat 400 includes a housing having a front surface 404 and at least one peripheral edge 508 that defines, at least in part, an opening (not shown) in the thermostat 400. A replaceable carbon monoxide sensor module 420 is provided, which is disposed adjacent to the thermostat 400. The replaceable carbon monoxide sensor module 420 has a portion that is configured to be removably received within the opening in the housing 404, so as to abut to the peripheral edge 408 of the thermostat 400 in a manner such that the replaceable carbon monoxide sensor module 420 is positioned against the peripheral edge 408 of the housing 404. In this manner, the replaceable carbon monoxide sensor module 420 and the thermostat housing 404 thereby form a single unit. Much like the above embodiments, the replaceable carbon monoxide sensor module 420 further includes a circuit board having a receptacle thereon, and a replaceable battery configured to be releasably received within the receptacle. On the circuit board is a replaceable carbon monoxide sensor that is configured to be releasably received within the receptacle in a manner that establishes electrical connection between the battery, the carbon monoxide sensor and the circuit board. The replaceable carbon monoxide sensor provides a measurable output value that is indicative of the level of carbon monoxide gas in the ambient air surrounding the thermostat, and continuous use of the sensor over an extended period of time causes the sensor's nominal output value to change substantially over time. The circuit board includes a microprocessor that is configured to activate a continuous audible alarm to indicate an emergency upon detecting a sensor output value indicative of a harmful level of carbon monoxide gas (a harmful level of carbon monoxide gas may be the presence of at least 300 parts per million of carbon monoxide gas, for example). The microprocessor is configured to monitor the replaceable carbon monoxide sensor and to activate an intermittent audible service alarm when the replaceable carbon monoxide sensor has exceeded a predetermined duration of use, to thereby prompt a user to remove and replace the replaceable carbon monoxide sensor module.

Accordingly, the microprocessor thereby prompts a user to replace the replaceable carbon monoxide sensor module 420 with a new carbon monoxide sensor module 420. The carbon monoxide sensor module 420 is releasably attached to the thermostat 400, to thereby allow for the removal of the carbon monoxide sensor module 420 for replacement thereof. In the thermostat 400 shown in FIG. 6, the replaceable carbon monoxide sensor module 420 is located on the thermostat 400 adjacent a peripheral edge 408 so as to form a single unit. This provides the advantage of including an integral or co-located replaceable carbon monoxide sensor module 420 for detecting the presence of carbon monoxide within the space that is being occupied by humans (rather than that of a basement or separate furnace/utility room). The replaceable carbon monoxide sensor module 420 also prompts the user to replace the replaceable carbon monoxide sensor module 420 upon determining that the carbon monoxide sensor is no longer reliable, such that the occupants are provided with reliable protection against the danger of carbon monoxide gas within the home.

Figure 7:
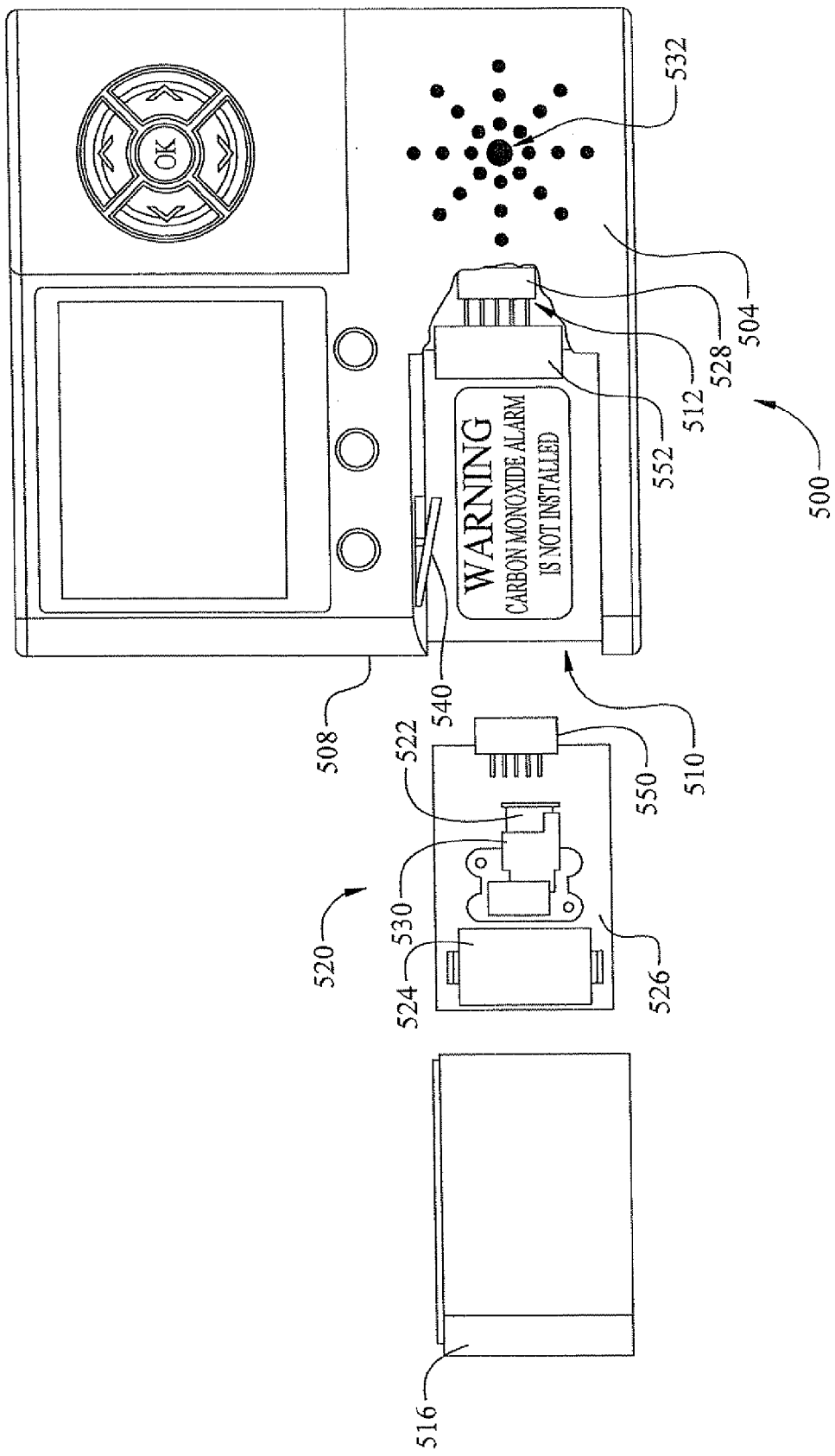
FIG. 7 is a perspective view of the carbon monoxide sensor components and thermostat of a fifth embodiment according to the principles of the present application.

Referring to FIG. 7, a fifth embodiment of a thermostat and replaceable carbon monoxide sensor is shown. The thermostat 500 includes a housing 504 having an opening in a peripheral side thereof, which provides access to the interior space of the thermostat, and a thermostat control circuit (not shown) within the housing 504 for controlling operation of at least a heating system. As shown in FIG. 7, the housing 504 has at least one peripheral portion 508 that, at least in part, defines an opening 510 in the thermostat 500, which provides access to the interior space 512 of the thermostat. The thermostat 500 further includes an access cover 516 for covering the opening 510 in the thermostat 500. The access cover 516 is removably attached to the thermostat 500, to thereby allow the access cover 516 to be removed to permit access to the interior space 512 of the thermostat 500.

The thermostat further includes a carbon monoxide sensor circuit comprising a circuit board 554 having a connector 552 thereon, the circuit board and connector 552 being disposed within the interior space 512 of the thermostat 500. The thermostat further includes a replaceable carbon monoxide sensor 522 and a battery 524 that applies a voltage to the replaceable carbon monoxide sensor 522. The replaceable carbon monoxide sensor 522 and battery 524 are configured to be to be removably inserted through the opening 510 into the interior space of the thermostat, and to be connected to the connector 544. The access cover 516 may also be connected to the circuit board 526 on which the battery 524 and replaceable carbon monoxide sensor 522 are disposed, and may be attached or connected simultaneously with the circuit board 526 to the thermostat 500.

The thermostat 500 further includes a carbon monoxide sensor 522 capable of sensing the presence of carbon monoxide gas in the ambient air near the thermostat 500. The carbon monoxide sensor 522 is configured to provide a measurable output of the sensed level of carbon monoxide gas that changes substantially with continuous use of the sensor over an extended period of time. The thermostat 500 also includes a replaceable battery 524 that applies a voltage to the carbon monoxide sensor 522. The thermostat 500 further includes a circuit board 526 that is inserted within the thermostat 500, adjacent the opening 510 in the thermostat cover 504. The circuit board 526 is configured to establish an electrical connection with the carbon monoxide sensor 522 and the battery 524, which electrical connection permits the circuit board 528 to monitor the output value of the carbon monoxide sensor 522. The circuit board 526 has a connector 550 that is configured to establish connection with the connector 552 of carbon monoxide sensor circuit 554. The circuit board 526 is configured to periodically read the carbon monoxide sensor output, and is further configured to activate a speaker 532 to provide an audible alarm in a continuous manner to indicate an emergency upon detecting an output value from the carbon monoxide sensor 522 that exceeds a predetermined value. The microprocessor 528 may also activate the emergency alarm where the sensor's output value changes by at least a 50 percent over a prior sensor output value received within a period of time of between about 15 to 90 minutes. The microprocessor 528, which is in communication with the carbon monoxide sensor 522, thus provides an audible emergency alarm signal to alert an occupant of the presence of a harmful level of carbon monoxide gas.

The thermostat further includes a detection means 540 for detecting when the replaceable carbon monoxide sensor component 520 is installed within the interior of the thermostat, and providing an input to the thermostat control circuit 554 when the replaceable carbon monoxide sensor is installed within the interior of the thermostat. The thermostat control circuit (not shown) disables operation of the heating system when the replaceable carbon monoxide sensor component 520 is not installed, to thereby ensure that the heating system is operated only when said replaceable carbon monoxide sensor is present.

The detection means 540 may comprise a mechanical switch activated by displacement of a lever 540, which is positioned within the interior space 512 of the thermostat, such that the lever 540 closes the switch only when the carbon monoxide sensor 522 and battery 524 are installed or received within the connector 530. Similarly, the switch could comprise a photo-optic emitter and collector positioned on opposite sides of the battery, for example, which would activate a switch when the battery is present between the emitter and collector. Alternatively, the thermostat 500 may employ a lever 540 that is displaced upon installation of the carbon monoxide sensor 522 and battery 524, where the cover 516 can only be attached upon displacement of the lever 540. The cover 516 could then cause a switch or electrical connection to occur upon attachment to the thermostat 500.

In the thermostat embodiment 500 shown in FIG. 7, the lever 540 preferably establishes electrical connection between the battery 524 and a thermostat control circuit associated with a circuit board 542. In this manner, the thermostat 500 would accordingly sense the presence of a voltage via the lever 540 when a battery 524 is received within the connector 530. When the carbon monoxide sensor 522 and battery 524 are installed (or alternatively when access cover 516 is attached), a switch or electrical connection occurs, which establishes a voltage that is detected by the control circuit associated with the circuit board 542 for controlling the thermostat's operation. The thermostat 500 enables heating operation only when this voltage is present and detected by the circuit board 542. Without installation of the carbon monoxide sensor 522 and battery 524, the disabled switch or lack of a connection would cause the thermostat to be incapable of operating the heating system. This ensures that a fuel-fired heating system would only be operated when a carbon monoxide sensor 522 and battery 524 have been installed, to provide for proper monitoring of carbon monoxide that may be produced by the fuel-fired heating system. Similarly, where the installed battery voltage is below a minimum detectable level, the thermostat control circuit associated with the circuit board 542 for controlling the thermostat 500 is configured to display a low battery indication and alter the temperature setting of the thermostat 500. The altered temperature setting may be a setting of 60 degrees Fahrenheit, for example, which would urge an occupant to check the thermostat and discover the display of a low level condition for the carbon monoxide sensor battery 524. Where the thermostat 500 does not detect the presence of a sufficient voltage via the electrical connection to the circuit board 542, the thermostat would not operate the heating system. This ensures that a fuel-Tired heating system would only be operated when the battery 524 associated with the carbon monoxide sensor 522 has a sufficient voltage level to provide for proper monitoring of carbon monoxide that may be produced by the fuel-fired heating system.

Accordingly, the thermostat 500 and replaceable carbon monoxide sensor 522 provide an additional function beyond that of the sensor's function of detecting a harmful level of carbon monoxide gas, in preventing operation of a heating system that could produce carbon monoxide gas unless a carbon monoxide sensor 522 and battery 524 with a sufficient voltage level are installed. This ensures that the heating system will only be operated during periods when the carbon monoxide sensor is present and operating, to thereby monitor for carbon monoxide that may be produced by the fuel-fired heating system, which function is not provided by other commercially available carbon monoxide sensors.

In the above embodiment, the microprocessor 528 may be further configured to activate an audible service alarm output upon detecting that the battery level is below a predetermined threshold. While the thermostat 500 depicted in FIG. 7 shows the replaceable carbon monoxide sensor 522 as being removable, alternatively, the circuit board 526, the replaceable carbon monoxide sensor 522 and battery 524 may all be removable through the opening 510, to thereby permit replacement of both the circuit board 526 and carbon monoxide sensor 522 together.

Figure 8:
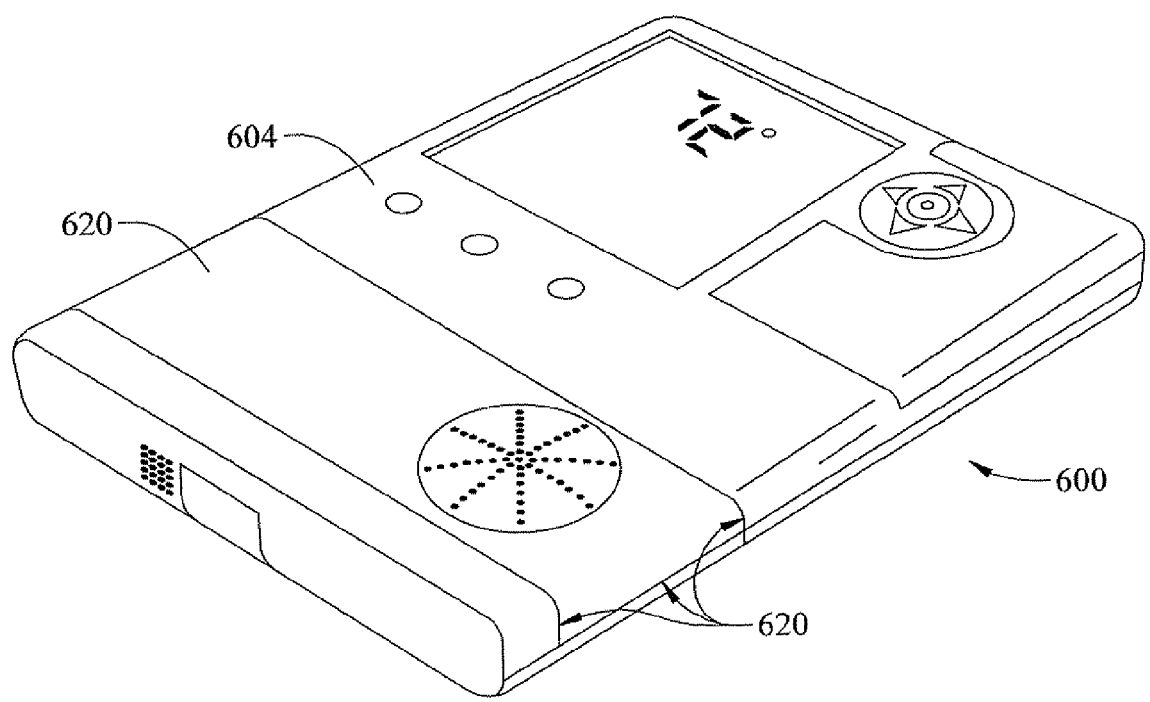
FIG. 8 is a perspective view of the carbon monoxide sensor components and thermostat of a fifth embodiment according to the principles of the present application.

In a sixth embodiment shown in FIG. 8, the thermostat 600 includes a housing 602 having a front surface 604 and at least one peripheral edge 608 that include, at least in part, openings on at least two sides (front and side) of the thermostat 600. The openings on at least two sides of the thermostat are configured to define a pocket or slot opening in the front of the thermostat. The pocket or slot opening extends horizontally across front of the thermostat 600, and a replaceable carbon monoxide sensor module 620 is disposed within the pocket/slot opening. The replaceable carbon monoxide sensor module 620 is configured to be removably received within the slot opening in the housing 602 in a manner such that the entire replaceable carbon monoxide sensor module 620 fits within the pocket opening/slot, and is flush with the front surface 604 and peripheral edge 608 of the housing 602. In this manner, the replaceable carbon monoxide sensor module 620 and the thermostat housing 602 thereby form a single unit. Much like the above embodiments, the replaceable carbon monoxide sensor module 620 further includes a circuit board having a receptacle thereon, and a replaceable battery configured to be releasably received within the receptacle. On the circuit board is a replaceable carbon monoxide sensor that is configured to be releasably received within the receptacle in a manner that establishes electrical connection between the battery, the carbon monoxide sensor and the circuit board. The replaceable carbon monoxide sensor provides a measurable output value that is indicative of the level of carbon monoxide gas in the ambient air surrounding the thermostat, and continuous use of the sensor over an extended period of time causes the sensor's nominal output value to change substantially over time. The circuit board includes a microprocessor that is configured to activate a continuous audible alarm to indicate an emergency upon detecting a sensor output value indicative of a harmful level of carbon monoxide gas (a harmful level of carbon monoxide gas may be the presence of at least 300 parts per million of carbon monoxide gas, for example). The microprocessor is configured to monitor the replaceable carbon monoxide sensor and to activate an intermittent audible service alarm when the replaceable carbon monoxide sensor has exceeded a predetermined duration of use, to thereby prompt a user to remove and replace the replaceable carbon monoxide sensor module.

Accordingly, the microprocessor thereby prompts a user to replace the replaceable carbon monoxide sensor module 620 with a new carbon monoxide sensor module 620. The carbon monoxide sensor module 620 is releasably attached to the thermostat 600, to thereby allow for the removal of the carbon monoxide sensor module 620 for replacement thereof. In the thermostat 600 shown in FIG. 6, the replaceable carbon monoxide sensor module 620 is located on the thermostat 600 flush with the front and the peripheral edge 608 so as to form a single unit. This provides the advantage of including an integral or co-located replaceable carbon monoxide sensor module 620 for detecting the presence of carbon monoxide within the space that is being occupied by humans (rather than that of a basement or separate furnace/utility room). The replaceable carbon monoxide sensor module 620, which includes a battery, a carbon monoxide sensor and a microprocessor in connection with the battery and carbon monoxide sensor, may be removed and replaced with a new replaceable carbon monoxide sensor module 620 that may include a microprocessor carbon monoxide sensor with newer technology so as to allow for upgrade of the module disposed on the thermostat 600. The replaceable carbon monoxide sensor module 620 also prompts the user to replace the replaceable carbon monoxide sensor module 620 upon determining that the carbon monoxide sensor is no longer reliable, such that the occupants are provided with reliable protection against the danger of carbon monoxide gas within the home.

It will be understood by those skilled in the art that the above thermostat and separate carbon monoxide sensor module located on the thermostat may be employed in various types of thermostats with any combination of the above disclosed features, without implementing the others. It will be understood that the thermostat and separate carbon monoxide sensor feature described above may be utilized in other forms of heating and cooling equipment, including remote temperature sensors. Accordingly, it should be understood that the disclosed embodiments, and variations thereof, may be employed in any type of thermostat or heating and cooling component.

What is claimed is:

1. A thermostat comprising:
a housing having at least one peripheral edge that includes an opening for providing access to an interior space of the thermostat;
an access cover for covering said opening, said access cover being removably attached to the thermostat to permit access to the interior space of the thermostat;
a circuit board associated with a carbon monoxide sensor circuit having a connector thereon, the circuit board being disposed within the interior space of the thermostat;
a replaceable carbon monoxide sensor configured to be connected to said connector, and to provide a measurable output that is indicative of the level of carbon monoxide gas in the ambient air surrounding the thermostat, where the replaceable carbon monoxide sensor provides a measurable output that changes substantially with continuous use of the sensor over time, said replaceable carbon monoxide sensor being configured to be removably inserted through said opening;
a battery that applies a voltage to said replaceable carbon monoxide sensor, said battery being configured to be removably inserted through said opening into the interior space of said thermostat;
a microprocessor disposed on a circuit board within the interior space of the thermostat, the circuit board being configured to establish an electrical connection with said replaceable carbon monoxide sensor and said battery, said microprocessor being configured to activate a continuous audible alarm to indicate an emergency upon detecting a sensor output that is indicative of a harmful level of carbon monoxide gas, wherein the microprocessor is configured to monitor use of the replaceable carbon monoxide sensor and to activate an intermittent audible service alarm when the replaceable carbon monoxide sensor has exceeded a predetermined duration of use, to thereby prompt a user to remove the access cover and replace the replaceable carbon monoxide sensor with a new replaceable carbon monoxide sensor;
a control circuit of the thermostat; and
a lever positioned within the interior space of the thermostat in a manner such that the lever is displaced when said replaceable carbon monoxide sensor and said battery are inserted through said opening, where the displacement of the lever establishes an electrical connection with the control circuit of the thermostat;
wherein the thermostat enables operation of a heating system only when an electrical connection is established with the control circuit, so as to prevent operation of said heating system unless said replaceable carbon monoxide sensor and said battery have been inserted within said thermostat, to thereby ensure that said heating system is operated only when said replaceable carbon monoxide sensor is present.

2. The thermostat of claim 1 wherein the control circuit is configured to sense the battery voltage level via the electrical connection and to detect when the battery voltage is below a minimum level, where the thermostat prevents operation of said heating system when said battery voltage is below a minimum level, to thereby ensure that said heating system is operated only when said battery that applies a voltage to said replaceable carbon monoxide sensor has sufficient voltage to provide for proper operation of the replaceable carbon monoxide sensor.

3. The thermostat of claim 1, wherein the microprocessor is further configured to activate an audible service alarm upon detecting that the carbon monoxide sensor's output value has changed by more than a predetermined amount relative to an output value of the replaceable carbon monoxide sensor obtained when the sensor first established electrical connection with the circuit board.

4. The thermostat of claim 1 wherein said circuit board is a stand-alone circuit board that is separate from any circuit of the thermostat, and further includes a receptacle configured to releasably receive the replaceable carbon monoxide sensor and battery in a manner that establishes electrical connection between the carbon monoxide sensor and battery and the circuit board.

5. A thermostat comprising:
a housing having at least one peripheral edge that defines, at least in part, an opening in the thermostat which provides access to an interior space of the thermostat;
a replaceable carbon monoxide sensor module that is disposed within the interior space of the thermostat, said replaceable carbon monoxide sensor module being configured to be removably received within the thermostat through said opening, the replaceable carbon monoxide sensor module including:
a circuit board having first and second receptacles thereon;
a replaceable battery configured to be releasable received within the first receptacle;
a replaceable carbon monoxide sensor configured to be releasable received within the second receptacle in a manner that establishes electrical connection between the battery, the carbon monoxide sensor and the circuit board, where the replaceable carbon monoxide sensor provides a measurable output value that is indicative of the level of carbon monoxide as in the ambient air surrounding the thermostat, and continuous use of the sensor over an extended period of time causes the sensor's nominal output value to change substantially over time;
a microprocessor disposed on the circuit board that is configured to activate a continuous audible alarm to indicate an emergency upon detecting a sensor output value indicative of a harmful level of carbon monoxide gas, wherein the microprocessor is configured to monitor the replaceable carbon monoxide sensor and to activate an intermittent audible service alarm when the replaceable carbon monoxide sensor has exceeded a predetermined duration of use, to thereby prompt a user to remove and replace the replaceable carbon monoxide sensor module;
a control circuit of the thermostat; and
a lever positioned within the interior space of the thermostat in a manner such that the lever is displaced when said replaceable carbon monoxide sensor and said battery are inserted through said opening, where the displacement of the lever establishes an electrical connection between the carbon monoxide sensor circuit and the control circuit of the thermostat;
wherein the thermostat enables operation of a heating system only when an electrical connection is established between the carbon monoxide sensor circuit and the control circuit, so as to prevent operation of said heating system unless said replaceable carbon monoxide sensor and said battery have been inserted within said thermostat, to thereby ensure that said heating system is operated only when said replaceable carbon monoxide sensor is present.

6. The thermostat of claim 5 wherein the control circuit is configured to sense the battery voltage level via the electrical connection and to detect when the battery voltage is below a minimum level, where the thermostat prevents operation of said heating system when said battery voltage is below a minimum level, to thereby ensure that said heating system is operated only when said battery that applies a voltage to said replaceable carbon monoxide sensor has sufficient voltage to provide for proper operation of the replaceable carbon monoxide sensor.

7. The thermostat of claim 6, wherein said access cover is releasably attached to the thermostat to permit access to the interior space, and the replaceable carbon monoxide sensor and battery are both removable through the opening, to thereby permit replacement of both the battery and sensor together.

8. The thermostat of claim 5 wherein the microprocessor is further configured to activate a continuous audible alarm upon detecting that the carbon monoxide sensor's output value has changed by more than a predetermined amount relative to a prior output value of the replaceable carbon monoxide sensor obtained when the sensor first established electrical connection with the circuit board.

9. The thermostat of claim 5 wherein said replaceable carbon monoxide sensor module has a stand-alone circuit board that is separate from any circuit of the thermostat, and further includes a cover portion for covering said opening.

10. The thermostat of claim 9 wherein a portion of the replaceable carbon monoxide sensor module and the cover portion attached thereto extend outside of said opening and protrude from the thermostat housing, to provide a grip portion for aiding in removal of said replaceable carbon monoxide sensor module.

11. A thermostat comprising:
a housing having a front surface and at least one peripheral edge that defines, at least in part, an opening in the thermostat;
a replaceable carbon monoxide sensor module that is disposed adjacent to the thermostat, said replaceable carbon monoxide sensor module having a portion that is configured to be removably received within said opening in the housing so as to attach to the peripheral edge of the thermostat in a manner such that the replaceable carbon monoxide sensor module is positioned against the peripheral edge of the housing to thereby form a single unit, the replaceable carbon monoxide sensor module including:
a circuit board having first and second receptacles thereon;
a replaceable battery configured to be releasably received within the first receptacle;
a replaceable carbon monoxide sensor configured to be releasably received within the second receptacle in a manner that establishes electrical connection between the battery, the carbon monoxide sensor and the circuit board, where the replaceable carbon monoxide sensor provides a measurable output value that is indicative of the level of carbon monoxide gas in the ambient air surrounding the thermostat, and continuous use of the sensor over an extended period of time causes the sensor's nominal output value to change substantially over time;
a microprocessor disposed on the circuit board that is configured to activate a continuous audible alarm to indicate an emergency upon detecting a sensor output value indicative of a harmful level of carbon monoxide gas, wherein the microprocessor is configured to monitor the replaceable carbon monoxide sensor and to activate an intermittent audible service alarm when the replaceable carbon monoxide sensor has exceeded a predetermined duration of use, to thereby prompt a user to remove and replace the replaceable carbon monoxide sensor module;
a control circuit of the thermostat; and
a lever positioned within the interior space of the thermostat in a manner such that the lever is displaced when said replaceable carbon monoxide sensor and said battery are inserted through said opening, where the displacement of the lever establishes an electrical connection between the carbon monoxide sensor circuit and the control circuit of the thermostat;
wherein the thermostat enables operation of a heating system only when an electrical connection is established between the carbon monoxide sensor circuit and the control circuit, so as to prevent operation of said heating system unless said replaceable carbon monoxide sensor and said battery have been inserted within said thermostat, to thereby ensure that said heating system is operated only when said replaceable carbon monoxide sensor is present.

12. The thermostat of claim 11 wherein the control circuit is configured to sense the battery voltage level via the electrical connection and to detect when the battery voltage is below a minimum level, where the thermostat prevents operation of said heating system when said battery voltage is below a minimum level, to thereby ensure that said heating system is operated only when said battery that applies a voltage to said replaceable carbon monoxide sensor has sufficient voltage to provide for proper operation of the replaceable carbon monoxide sensor.

13. The thermostat of claim 11 wherein the microprocessor is further configured to activate a continuous audible alarm upon detecting that the carbon monoxide sensor's output value has changed by more than a predetermined amount relative to a prior output value of the replaceable carbon monoxide sensor obtained when the sensor first established electrical connection with the circuit board.

14. The thermostat of claim 11 wherein said replaceable carbon monoxide sensor module has a stand-alone circuit board that is separate from any circuit of the thermostat, and further includes a cover portion for covering said opening.

15. A thermostat comprising:
a housing having an opening in a peripheral side thereof, which provides access to an interior space of the thermostat;
a thermostat control circuit for controlling operation of at least a heating system;
a carbon monoxide sensor circuit comprising a circuit board having a connector thereon, the circuit board and connector being disposed within the interior space of the thermostat;
a replaceable carbon monoxide sensor and a battery that applies a voltage to said replaceable carbon monoxide sensor, the replaceable carbon monoxide sensor and the battery being configured to be removably inserted through said opening into the interior space of said thermostat, and to be connected to said connector on said circuit board, where the replaceable carbon monoxide sensor provides a measurable output of the sensed level of carbon monoxide gas that changes substantially with continuous use of the sensor over an extended period of time;
a microprocessor disposed on the circuit board that receives the output of the replaceable carbon monoxide sensor, said microprocessor activating an audible emergency alarm upon detecting a sensor output indicative of a harmful level of carbon monoxide gas, and an audible intermittent service alarm when the replaceable carbon monoxide sensor has exceeded a predetermined duration of use to thereby prompt a user to remove and replace the replaceable carbon monoxide sensor module,
a detection means for detecting when the replaceable carbon monoxide sensor is installed within the interior of the thermostat and providing an input to the thermostat control circuit when the replaceable carbon monoxide sensor is installed within the interior of the thermostat, wherein the thermostat control circuit disables operation of the heating system when the carbon monoxide sensor is not installed, to thereby ensure that the heating system is operated only when said replaceable carbon monoxide sensor is present;
wherein the detection means comprises a lever positioned within the interior space of the thermostat in a manner such that the lever is displaced when said replaceable carbon monoxide sensor and said battery are inserted through said opening, where the displacement of the lever establishes an electrical connection between the carbon monoxide sensor circuit and the thermostat control circuit to provide an input to the thermostat control circuit.

* * * * *